United States Patent
Kizilel et al.

(10) Patent No.: US 10,022,446 B2
(45) Date of Patent: Jul. 17, 2018

(54) PH RESPONSIVE HYBRID HYDROGEL AND METHOD OF SYNTHESIS THEREOF

(71) Applicant: KOç ÜNIVERSITESI, Istanbul (TR)

(72) Inventors: Seda Kizilel, Istanbul (TR); Ozlem Cevik, Istanbul (TR)

(73) Assignee: KOç ÜNIVERSITESI, Istanbul (TR)

( * ) Notice: Subject to any disclaimer, the term of this patent is extended or adjusted under 35 U.S.C. 154(b) by 12 days.

(21) Appl. No.: 15/503,716

(22) PCT Filed: Aug. 22, 2014

(86) PCT No.: PCT/TR2014/000289
§ 371 (c)(1),
(2) Date: Feb. 14, 2017

(87) PCT Pub. No.: WO2016/028238
PCT Pub. Date: Feb. 25, 2016

(65) Prior Publication Data
US 2017/0266291 A1   Sep. 21, 2017

(51) Int. Cl.
*A61K 47/32* (2006.01)
*A61K 31/197* (2006.01)
*C08F 257/00* (2006.01)
*A61K 9/00* (2006.01)

(52) U.S. Cl.
CPC ............ *A61K 47/32* (2013.01); *A61K 9/0024* (2013.01); *A61K 31/197* (2013.01); *C08F 257/00* (2013.01)

(58) Field of Classification Search
CPC .... A61K 47/32; A61K 9/0024; A61K 31/197; C08F 257/00

USPC ......................................................... 514/561
See application file for complete search history.

(56) References Cited

U.S. PATENT DOCUMENTS

2004/0198822 A1   10/2004 Fraser et al.

OTHER PUBLICATIONS

Anthony M Lowman et al:"Analysis of the complexation/decomplexation phenomena in graft copolymer networks", Macromolecules, vol. 61, Aug. 25, 1997 (Aug. 25, 1997), pp. 4959-4965, XP002738936, p. 4959-p. 4965.
Cody A Schoener et al:"pH-responsive hydrogels with dispersed hydrophobic nanoparticles for the delivery of hydrophobic therapeutic agents", Polymer International, vol. 61, Apr. 11, 2012 (Apr. 11, 2012), pp. 874-879, XP002738937, DOI: 10.1002/PI.4219 the whole document.
Schoener CA, Hutson HN, Pappas NA. J:"pH-Responsive Hydrogels with Dispersed Hydrophobic Nanopartioles for the Oral Delivery of Chemotherepeutics", Biomed Mater Res Part A, vol. 101, 2012, pp. 2229-2236, DOI: 10.1002/jbm.a.34532.

*Primary Examiner* — Yevgeny Valenrod
(74) *Attorney, Agent, or Firm* — Gokalp Bayramoglu (57) ABSTRACT

A pH-responsive hybrid hydrogel, namely poly(Methacrylic acid-grafted-Ethylene Glycol) P(MAA-g-EG) cross-linked with Styrene-Butadiene-Styrene (SBS) polymer and photopolymerized by visible light. The resulting polymer turned out to have better integrities, high swelling ratios, pH-responsive and biocompatible character. Also the visible-light-induced synthesis of these pH-responsive composite wherein eosin Y is used as photoinitiator and triethanolamine is used as a co-initiator is also disclosed in the invention.

19 Claims, 7 Drawing Sheets

PH RESPONSIVE HYBRID HYDROGEL AND METHOD OF SYNTHESIS THEREOF

CROSS REFERENCE TO RELATED APPLICATIONS

This application is the national phase entry of International Application No. PCT/TR2014/000289, filed on Aug. 22, 2014, the entire contents of which is incorporated herein by reference

TECHNICAL FIELD

The present invention is related to a pH responsive hybrid hydrogel, namely styrene-butadiene-styrene (SBS) incorporated poly(methacrylic acid-grafted-Ethylene Glycol) P(MAA-g-EG) hydrogel synthesized via visible light photopolymerization.

BACKGROUND OF THE INVENTION

Effective and efficient delivery of drugs is an important area of research in pharmaceutical industry due to the significant challenges related to the physiological properties of therapeutics. For example, biomolecular therapeutics degrade by proteolytic enzymes and hence can only remain in the plasma circulation for a short period of time therefore higher dose use is required. In order to overcome those and such problems functional and responsive polymeric network structures as delivery vehicles for controlled drug release are being developed. And sequential delivery of drugs with altered hydrophobicities is achieved via responsiveness to specific stimuli. Polymeric hydrogels are attracting special attention due to their biocompatible character, capacity to retain water, and permeable structures. As a result they have been increasingly used in biomedical and pharmaceutical applications including drug delivery systems. Stimuli responsive hydrogel networks also referred as smart materials can exhibit desirable physicochemical properties depending on their collapsed or swollen states. These properties change significantly in response to changes in environmental properties such as elevated temperatures, wavelength of light, electric field, ionic strength and pH. Particularly, pH sensitive hydrogels can detect changes in environmental pH that causes corresponding, modification on the physical properties of hydrogels such as shape and size. pH sensitive hydrogels are specifically useful for oral administration of the drug along the digestive tract due to the drastically different pH conditions observed at different locations, or for targeted drug delivery into tumor site due to alterations in the acidity of the tumor tissues.

Poly(methacrylic acid-grafted-Ethylene Glycol) (P(MAA-g-EG)) hydrogels are known to be used as pH responsive polymeric networks. And also in prior art, there are studies regarding to functionalization of P(MAA-g-EG) hydrogels, especially for sequential delivery of therapeutics. A combination of a stimuli responsive hydrophilic network with a less hydrophilic component might have the potential to provide site specific and sustained drug delivery. For example, in a study by Schomer et al. that was published in 2012, light mediated polymerization is used for the synthesis of both P(MAA-g-EG) hydrogels dispersed with poly methylmethacrylate) (PMMA) nanoparticles and amphiphilic interpenetrating networks (IPNs) of P(MAA-g-EG) and poly (n-butyl acrylate) PBA and their use as the oral drug delivery agents for pharmaceutical use was enclosed in the study as well. (Schomer C A, Hutson H N, Peppas N A. J Biomed Mater Res Part A 2012; 101:2229-36.) Photoinitiated free radical polymerization using UV light is a widely used method for the synthesis of P(MAA-g-EG) hydrogels. Although this method works efficiently, high amounts of photo initiators and co-initiators are being used which affects the biocompatible character of the resulting hydrogel.

It is apparent that there is a substantial need for a biocompatible, functionalized, effective, responsive hybrid hydrogels to be used in drug delivery applications and an efficient way of synthesizing such hydrogels. Here, in this invention visible light induced photopolymerization of pH responsive composite P(MAA-g-EG) hydrogel is suggested as a drug delivery vehicle for controlled release applications and by this method lesser amount of initiator is used and shorter reaction time is realized. The resulting polymer is functional, has improved integity, enhanced biocompatibility and advanced swelling properties.

SUMMARY OF THE INVENTION

One aspect of the invention is directed to a pH responsive hybrid hydrogel, namely Styrene-Butadiene-Styrene (SBS) incorporated poly(Methacrylic acid-grafted-Ethylene Glycol) P(MAA-g-EG), that is synthesized through photopolvmerization induced by visible light in the presence of a photo-initiator and a co-initiator. In a selected embodiment of the invention the photo-initiator is selected to be Eosin Y and the co-initiator is selected to be Triethanolamine (TEA). In a preferred embodiment of the invention, the incorporated SBS is selected to be either in disc form or in crushed particle form. The resulting P(MAA-g-EG) hydrogel turned out to be a functional hydrogel with improved integrity, advanced swelling properties, enhanced swelling properties with less toxicity.

Figure 2:
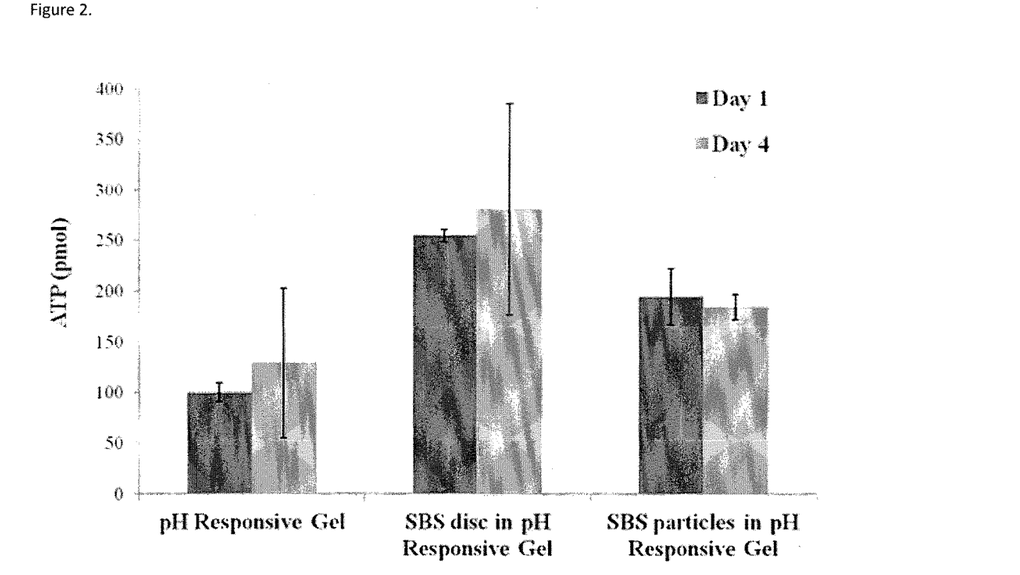
FIG. 2. In vitro cell viability assay results, (ATP amounts for visible light induced pH responsive P(MAA-g-EG) hydrogel: disc SBS incorporated P(MAA-g-EG) hybrid hydrogel and particle SBS incorporated P(MAA-g-EG) hybrid hydrogel.

Another aspect of the invention is the method of synthesizing a pH responsive hybrid hydrogel, SBS incorporated poly(Methacrylic acid-grafted-Ethylene Glycol) P(MAA-g-EG) by visible light induction. In a preferred embodiment of the invention, Eosin Y is used as the photo-initiator and Triethanolamine (TEA) is used as the co-initiator in the disclosed method of synthesis. And in a more preferred embodiment of the invention the method of synthesizing P(MAA-g-EG) hydrogel is characterized with the following steps i. The monomers methacrylic acid (MAA) and poly (ethylenglycol) monomethyl ether monomethacrylate (PEGMMA) and the crosslinking agent tetraetylene glycol dimethacrylate (TEGDMA) is mixed and the photo-initiator triethanolamine and a co-initiator eosin Y are added to the solution and ii. Styrene-butadiene-styrene (SBS) either in disc form or crushed form is added to the mixture and shaken iii. the resulting solution is then exposed to visible light and iv. finally washed with water and finally freeze dried Cytotoxicity levels of the hydrogel that is obtained via the method of synthesis described in this invention is proved to be comparatively low via cell viability tests. In vitro Cell Viability tests were done with Mouse 3T3 fibroblasts and the fibroblasts were analyzed after 1 and 4 days of incubation. Best fibroblast viability was observed in the sample of pH responsive hydrogel with SBS particles. (as shown in FIG. 2.) Also, irritation and intracutaneous reactivity of the resulting hydrogel is tested and had been demonstrated that the hybrid hydrogels did not result in any intracutaneous reaction such as erythema and edema in rabbits which is a significant indication about the biocompatibility of pH responsive hydrogels synthesized with the approach developed here.

This invention enclosed in this application is the first example to visible light photopolymerized hybrid p(MAA-g-EG) hydrogel and the method of synthesis thereof. It is also proved that the method of synthesis enclosed in this invention is advantageous over UV-light initiated photopolymerization since less amount of photo-initiator is used and the reaction time is also shorter. The resulting p(MAA-g-EG) hydrogel is proved to have enhanced swelling behavior, and since less amount of initiator is employed, the resulting hydrogel becomes less toxic hence more biocompatible. These properties make the hydrogel a good candidate for pharmaceutical applications especially for controlled release applications.

DETAILED DESCRIPTION OF THE INVENTION

The main aspect of the invention is a novel pH responsive hybrid hydrogel, namely Styrene-Butadiene-Styrene (SBS) incorporated poly (M acid-grafted-Ethylene Glycol) p(MAA-g-EG), which is synthesized via visible light induced photopolymerization. In a preferred embodiment of the invention Eosin Y is used as the photo-initiator and Triethanolamine (TEA) is used as the co-initiator for the synthesis of aforementioned pH responsive hybrid hydrogel.

In another aspect of the invention, the incorporated SBS is added to poly(Methacrylic acid-grafted-Ethylene Glycol) p(MAA-g-EG) prepolymer solution either in the disc form or in crushed particle form.

In a preferred embodiment of the invention, pH responsive hybrid hydrogel as described above wherein the method of synthesis is characterized by a process comprising the following steps
  i. The monomers methacrylic acid (MAA) and poly (ethylenglycol) monomethyl ether monomethacrylate (PEGMMA) and the crosslinking agent tetraetylene glycol dimethacrylate (TEGDMA) is mixed and the photo-initiator triethanolamine and a co-initiator eosin Y are added to the solution and
  ii. Styrene-butadiene-styrene (SBS) either in disc for crushed form is added to the mixture and shaken
  iii. the resulting solution is then exposed to visible light and
  iv. finally washed with water and freeze dried.

Another aspect of the invention is a method of synthesizing a pH responsive hybrid hydrogel, namely Styrene-Butadiene-Styrene (SBS) incorporated poly(Methacrylic acid-grafted-Ethylene Glycol) p(MAA-g-EG) via visible light induced photopolymerization. In a preferred embodiment of the invention, Eosin Y is used as the photo-initiator and Triethanolamine (TEA) is used as the co-initiator in the said method.

In a preferred embodiment of the invention the SBS is added to the p(MAA-g-EG) prepolymer solution either in disc form or crushed particle form in the aforementioned method of synthesis of the hybrid polymer.

In the preferred embodiment of the invention the method of synthesizing the pH responsive hybrid hydrogel is characterized by a process comprising the following steps
  i. The monomers methacrylic acid (MAA) and poly (ethylenglycol) monomethyl ether monomethacrylate (PEGMMA) and the crosslinking agent tetraetylene glycol dimethacrylate (TEGDMA) is mixed and the photo-initiator triethanolamine and a co-initiator eosin Y are added to the solution and
  ii. Styrene-butadiene-styrene (SBS) either in disc form or crushed form is added to the mixture and shaken
  iii. the resulting solution is then exposed to visible light and
  iv. finally washed with water and freeze dried Another aspect of the invention is the use of the pH responsive hybrid hydrogel described before for drug delivery applications such as controlled release, sustained release or sequential release.

Another aspect of the invention is a pharmaceutical composition comprising the disclosed pH responsive hybrid hydrogel, an active ingredient and pharmaceutically acceptable excipients. In a preferred embodiment of the invention the active ingredient is selected from a group of anticonvulsant drugs comprising gabapentin, lamotrigine, levetiracetam, oxcarbazepine, pregabalin, tiagabine, topiramate and zonisamide and most preferably the active ingredient is selected to be pregabalin.

Disclosed pharmaceutical composition is selected to be in the form of a tablet, capsule, intravenous formulation, intranasal formulation, transdermal formulation, formulation for muscular injection, syrup, suppository or aerosol.

Hydrogels as used here in this invention refers to hydrophilic polymer chains those may be either natural or synthetic polymers and are capable of absorbing high amounts of water. Hydrogels find a wide range of application areas such as targeted drug delivery, tissue engineering, biosensors, and diapers as such.

pH-responsive hydrogels with the definition as used in the this invention refers to hydrogels that are capable of detecting environmental pH changes that cause a corresponding modification on the physical properties of the polymer such as shape and size and as a result of this change they release the load they have. This type of hydrogels are also known as "smart" or "intelligent" gels since they are capable of sensing the environmental changes, in this case pH changes there are also other types of hydrogels that are responsive to other environmental changes such as temperature, concentration and as such. "Hybrid hydrogels" are defined as the hydrogels that are assembled from at least 2 different types of polymeric systems.

"Styrene-Butadiene-Styrene (SBS) in disc form" refers to SBS discs as synthesized with respect to the method detailed in this description; and "Styrene-Butadiene-Styrene (SBS) in crushed form" refers to shredded form of SBS and obtained by shredding the disc form.

The active ingredient or a pharmaceutical formulation containing the active ingredient may be administered whether systemically or at the site including but not limited to oral, topical, pulmonary, rectal, vaginal, and parenteral.

It is preferable to formulate an active ingredient as a pharmaceutical composition comprising at least one active ingredient together with one or more pharmaceutically acceptable excipients such as carriers, fillers, diluents, buffers, adjuvants, stabilizers, or other materials.

The formulations may be prepared by any method known in the pharmaceutical literature and may be presented in unit dosage form. Formulations may be in the following forms but not limited to tablets, capsules, syrup, lozenges, pills, cachets, sachets, pills, ointments, gells, creams, sprays, pastes, aerosols or suppositories.

EXAMPLES

The following examples are provided to illustrate the present invention and are not intended to limit the scope of the invention.

Example 1

Synthesis of hybrid SBS incorporated poly(Methacrylic acid-grafted-Ethylene Glycol) P(MAA-g-EG)

Figure 1:
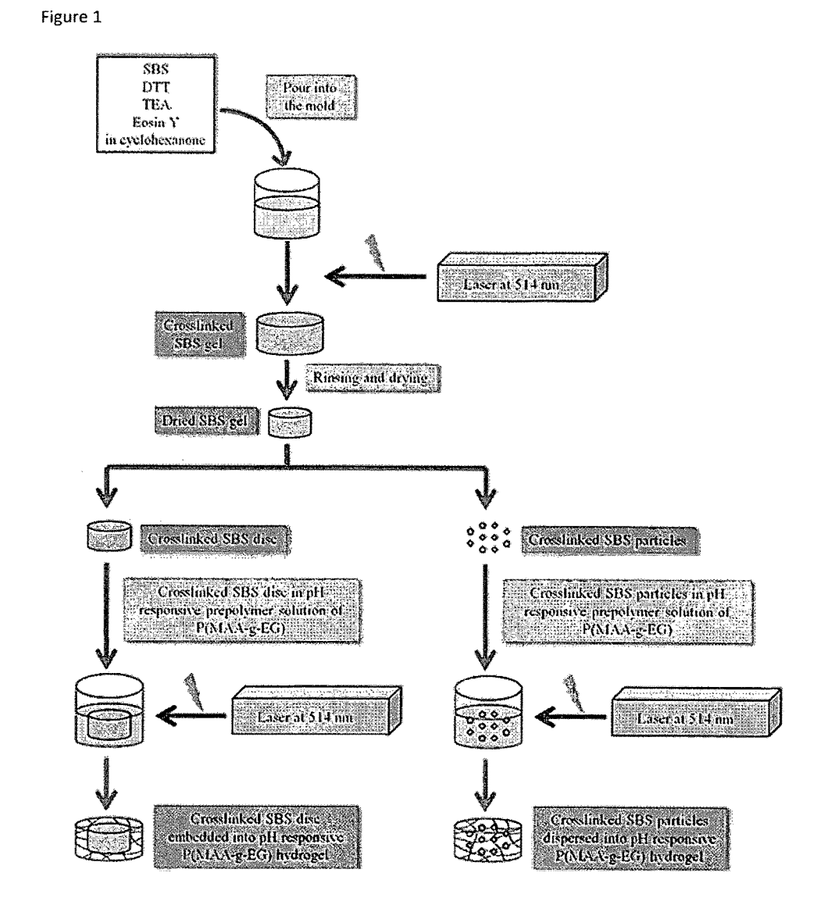
FIG. 1. Scheme for synthesis of hymphobic SBS formation and its subsequent encapsulation within pH responsive hydrogels.

The P(MAA-g-EG) prepolymer solution consisted of 3.6 g of MAA and 2.0 g of PEGMMA, and 0.5 mol % TEGDMA. Next,. 225 mm TEA and 0.03 mM eosin Y were added into the prepolymer solution, which included 50:50 (w/w) solution of ethanol and water mixture. Then, crosslinked SBS iii the form of disc and shredded particles were added into the prepolymer solution, shaken at 120 rpm for 24 h. Next, the solution was exposed to green light (514 nm and 7.5 mW/cm$^2$) using argon laser for 20 min. Finally, hybrid gels were rinsed with distilled water for several days and freeze-dried. (FIG. 1)

Example 2

Dynamic weight swelling experiments for hybrid P(MAA-g-EG) on alternating pH conditions Dynamic weight swelling experiments were carried out in different pH solutions in order to further characterize pH sensitivity of the hydrogel. DMGA buffer solutions at 0.1 M and with a range of pH 3.8 to pH 7.0 were used at 37° C. The hydrogel was kept in DMGA buffer solution with a specific pH and weighed at specified time intervals for the calculation of equilibrium weight swelling ratio. The weight swelling ratio, q represents the swelling ratio of the network and was calculated using the following equation:

$$q = \frac{W_s}{W_d}$$

where $W_s$ is the weight of the swollen hydrogel and $W_d$ is the initial weight of the dried hydrogel. Reversible swelling/deswelling behavior of all types of hydrogels was characterized using 0.1 M DMGA buffer solutions with pH values within 2.2-7.0 range at 37° C. For these experiments, ionic strength of DMGA buffers were maintained with sodium chloride and the temperature of the medium was kept at 37° C.

Figure 3:
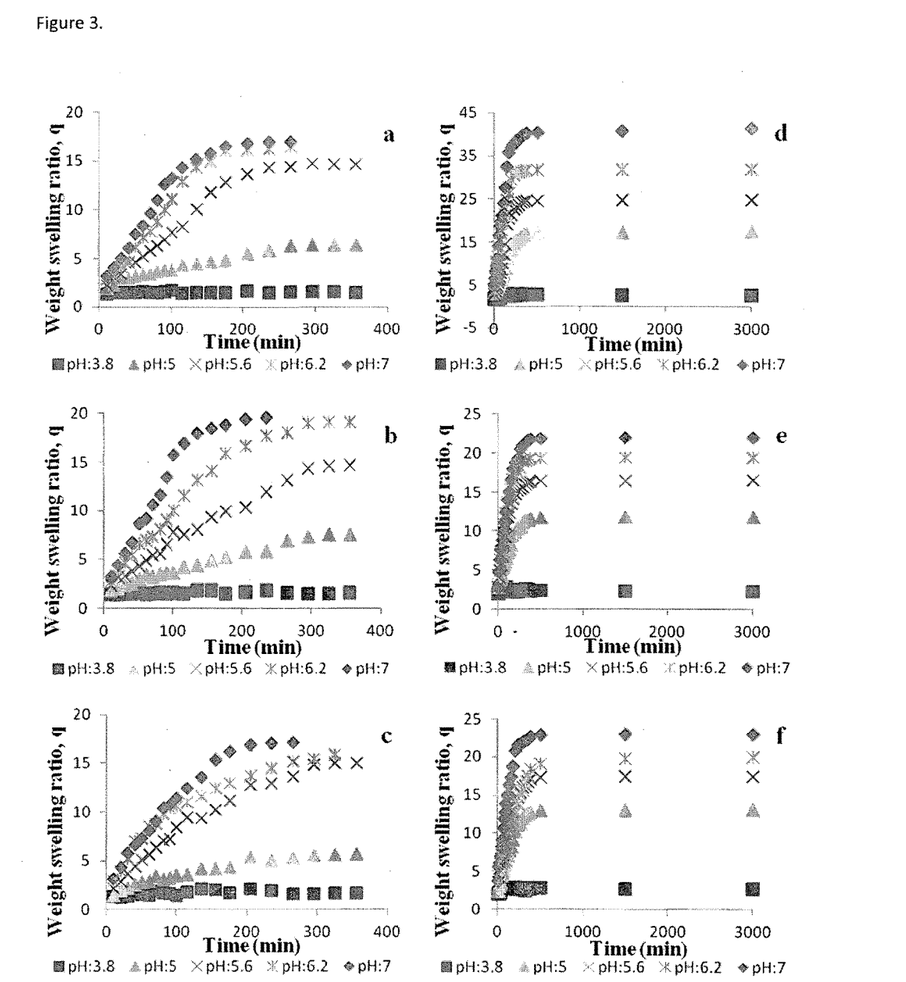
FIG. 3. Dynamic swelling behavior of (a) pH responsive hydrogel P(MAA-g-EG) (b) crosslinked SBS disc embedded into P(MAA-g-EG) hydrogel, (c) crosslinked SBS particles dispersed into P(MAA-g-EG) hydrogel that were photopolymerized under UV light. Dynamic swelling/deswelling behavior of (d) pH responsive hydrogel P(MAA-g-EG) (e) crosslinked SBS disc embedded into P(MAA-g-EG) hydrogel, (f) crosslinked SBS particles dispersed into P(MAA-g-EG) hydrogel that were photopolymerized under visible light.

For all dynamic swelling experiments, minimal swelling is observed in acidic condition while maximum swelling occurred in basic environment is reported. Hydrogels cured with visible light had higher swelling ratios compared to their UV photopolymerized counterparts. Swelling ratios as high as 37 could be obtained for P(MAA-g-EG) hydrogel synthesized with visible light, where this ratio was around 17 for hydrogels formed with UV light. The results revealed that incorporation of crosslinked SBS into the responsive hydrogels cured with UV light causes statistically not significant differences in swelling, where the ratios ranged between 15 and 20. However, this observation was not valid when light exposure wavelength was changed to visible range, and addition of crosslinked SBS into system in the form of disc or particles reduced swelling from 37 down to 22. (Shown in FIG. 3)

Figure 4:
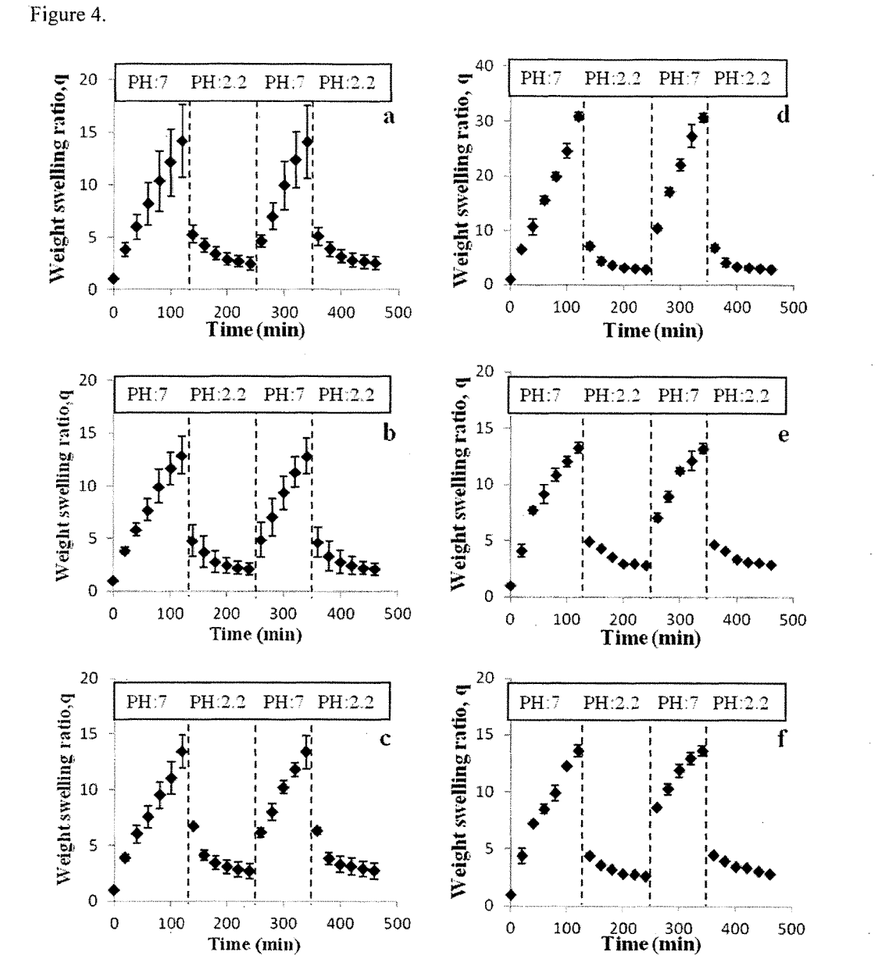
FIG. 4. Reversible swellingldeswelling behavior of (a) pH responsive hydrogel P(MAA-g-EG) (b) crosslinked SBS disc embedded into P(MAA-g-EG) hydrogel, (c) crosslinked SBS particles dispersed into P(MAA-g-EG) hydrogel which all had been photopolymerized under UV light. Reversible swellingideswelling behavior of (d) pH responsive hydrogel P(MAA-g-EG) (e) crosslinked SBS disc embedded into P(MAA-g-EG) hydrogel, (f) crosslinked SBS particles dispersed into P(MAA-g-EG) hydrogel which all had been photopolymerized under visible light.

Reversibility of swelling was also tested for hydrogels formed with both UV and visible light cured hydrogels through incubation of samples at low pH (pH:2.2) and high pH (pH:7.0) buffets (Shown in FIG. 4). It was observed that, hydrogels synthesized under different conditions can all respond to repeated changes in pH, where highest swelling was obtained for P(MAA-g-EG) hydrogel cured under visible light. Addition of crosslinked SBS disc or particles into the P(MAA-g-EG) hydrogels influenced weight swelling ratios significantly, where lower swelling weight ratios were obtained when visible light exposure was used.

Example 3

Loading and release studies of pregabalin on hyrid hydrogels

Pregabalin loading studies were carried out with visible light cured P(MAA-g-EG) hydrogels. P(MAA-g-EG) hydrogels were incubated for 16 hours in 10 ml pregabalin stock solution, which was prepared in 1×PBS (pH 7.4) at a concentration of 0.25 mg/ml. Next, hydrogels were collapsed with the addition of 2 μl of 6 M HCl in order to keep the drug within the network. In order to eliminate any drug adsorption on the surface, pregabalin-loaded hydrogels were rinsed with distilled water.

UV-visible spectrophotometer at 210 nm wavelength was used to measure pregabalin absorption. Standard calibration curve for the absorption of pregabalin in aqueous solution was generated for determination of concentration in unknown samples. Loading efficiency of pregabalin into hybrid gels was calculated as follows:

$$\text{Loading Efficiency} = \frac{M_0 - M_f}{M_f} * 100 \quad (2)$$

where $M_o$ represents pregabalin mass in the stock solution initially and $M_f$ is the final pregabalin mass remaining in the solution at the end of 16 hours.

Pregabalin-loaded hydrogels were placed in 1×PBS (pH 7.4) at 100 rpm and 37° C. for release experiments. For every 30 minutes up to 7 hours, 500 µl samples were taken and replaced with 1×PBS (pH:7.4) to sustain sink conditions. The same experiment was repeated at low pH conditions, where the solution buffer was replaced with 1×PBS at a pH of 2. Pregabalin concentrations obtained from absorption measurements were used to calculate mass released at time t ($M_t$) using the following equation:

$$M_t = C_t * V + \Sigma C_{t-1} * V_s \quad (3)$$

where $C_t$ is the concentration of pregabalin in the release solution at time t, V is the total volume of release solution (10 ml) and $V_s$ is the sample volume that is taken (500 µl). Using the $M_t$ values, the % release of pregabalin was determined as expressed with the following equation:

$$\% \text{ Mass Released} = \frac{M_t}{M_\infty} * 100 \quad (4)$$

where $M_\infty$ is the total weight of pregabalin released during the experiment. Once the diffusion behavior of pregabalin from pH responsive and hybrid hydrogels were obtained, the results were modeled using the power-law correlation:

$$\frac{M_t}{M_\infty} = kt^n \quad (5)$$

where k represents the characteristic constant of the hydrogel and n is the exponential coefficient, which describes the mode of transport mechanism. The value of n has been found reported as 0.45 for Fickian Diffusion and 0.89 for swelling-controlled diffusion for cylindrical geometry. The fittings were done based on the first 60% of the collected release data to obtain a more accurate fit.

PGB loading and release experiments were carried out with P(MAA-g-EG) hydrogels synthesized with visible-light-induced polymerization. Depending oil the network structure and composition of hybrid hydrogels different PGB loading efficiencies were obtained. For example, PGB was loaded as 56.67+8.34%, 62.29+1.72% and 63.48+2.35% into P(MAA-gEG), SBS disc incorporated P(MAA-g-EG), and SBS particle incorporated P(MAA-g-EG) hydro tel, respectively [Table 1]. Slightly higher levels of loading efficiencies were obtained when SBS was added into the responsive network.

TABLE 1

Loading efficiency of pregabalin into visible light cured hydrogels.

| Formulation of Hydrogel | % Loading Efficiency | Weight Swelling Ratio |
| --- | --- | --- |
| Pure P(MAA-g-EG) | 56.67 ± 8.34 | 40 |
| SBS disc embedded into P(MAA-g-EG) | 62.29 ± 1.72 | 22 |
| SBS particles into P(MAA-g-EG) | 63.48 ± 2.35 | 23 |

Figure 5:
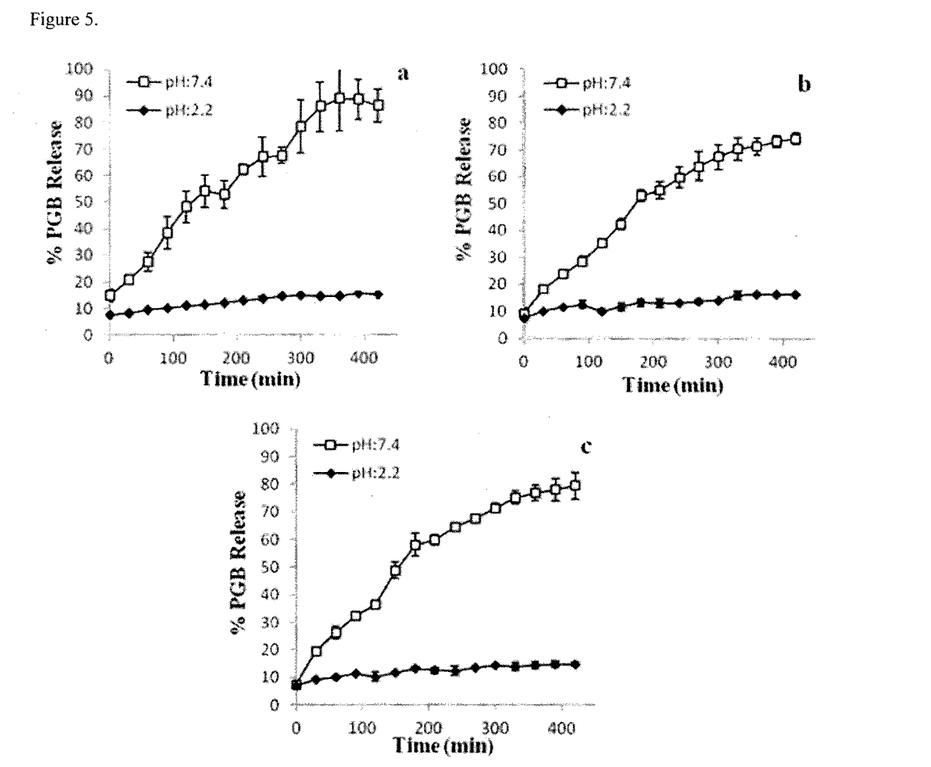
FIG. 5. Release behavior of pregabalin at pH=2.2 and pH=7.0 from (a) pH responsive P(MAA-g-EG) hydrogel, (b) SBS embedded into P(MAA-g-EG) hydrogel, and (c) SBS particles dispersed into P(MAA-g-EG) hydrogel that were photopolymerized under visible light.

Drug release studies were carried out at constant pH medium where drug release profiles were observed for different hydrogel samples. In neutral pH environment, 86.37% of PGB was released from hydrophilic pH responsive P(MAA-g-EG) hydrogel within 400 minutes, whereas in acidic pH only 15.32% of PGB release was observed [Shown in FIG. 5(a)]. FIGS. 5b and 5c demonstrates a decreased PGB release from composite pH responsive hydrogels compared to pH responsive P(MAA-g-EG) hydrogel. At high pH condition, 74.31% PGB was released from P(MAA-g-EG) hydrogels having crosslinked SBS disc inside, whereas at low pH only 16.37% PGB was released from the network (Shown in FIG. 5(b)).

Figure 6:
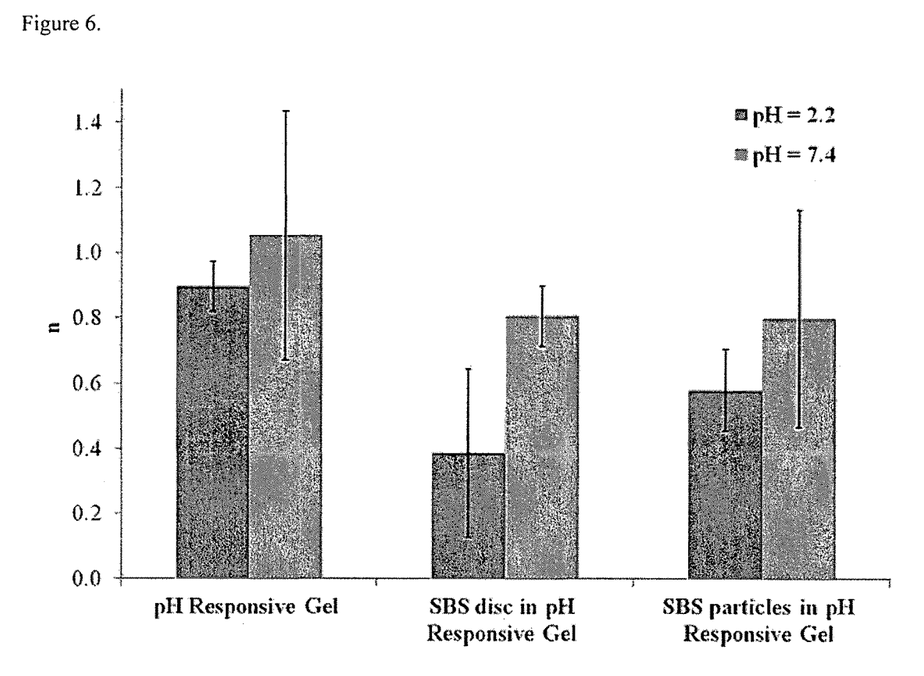
FIG. 6. The values of power law coefficient (n) for pH responsive P(MAA-g-EG) hydrogel and its composite forms at pH=2.2 and pH=7.0.

When crosslinked SBS particles were introduced into the pH sensitive hydrogel, 79.53% and 14.85% of the drug was released at pH:7.4 and at pH:2.2, respectively (Shown in FIG. 5(c)). The transport of PGB from each hydrogel sample (pure pH-responsive, SBS disc embedded and SBS particle containing) was modeled using equation (5). Exponent n in the equation describes the mode of transport, and was determined for each condition at high (pH:7.4) and low (pH:2.2) pH conditions. Values of n closer to 0.45 designate a Fickian mode of diffusion, whereas values closer to 0.89 designate a swelling-controlled diffusion behavior. It was observed that the values of n were lower for to pH conditions for all types of gels (As shown in FIG. 6). This is expected as the pH sensitive P(MAA-g-EG) collapses at this condition and thus the transport of PGB is likely to be dominated by Fickian diffusion (Shown in FIG. 6). Moreover, SBS-containing gels exhibited lower n values meaning Fickian diffusion forces were more dominant both at lower and higher pH values compared to the diffusion through pure P(MAA-g-EG) hydrogel. The diffusion behavior was found to be similar for SBS disc-embedded and SBS particle containing hybrid gels, however the disk embedded hybrid hydrogels exhibited a lower n value at low pH. Percent PGB release was decreased with addition of crosslinked SBS gel into the hydrophilic pH sensitive P(MAA-g-EG) network. As hydrophobicity of P(MAA-g-EG) hydrogels increase with addition of SBS disc or particles, PGB release from hybrid hydrogels was decreased as shown in FIG. 5. Additionally, hybrid hydrogels containing SBS particles exhibited slightly higher levels of PGB release compared to the other type of hybrid hydrogels containing an. SBS disc (FIG. 5(b,c)).

Example 4

In vitro cell viability experiments for hybrid P(MAA-g-EG) hydrogels

To investigate in vitro cell viability of hybrid hydrogels, mouse fibroblast 3T3 cell lines were used. Cells were cultured at 37° C. with 5% $CO_2$ in an incubator and maintained in Dulbecco Modified Eagle's Medium DMEM which was supplemented with 1% Penicillin/Streptomycin, 2 mM L-Glutamin and 10% fetal bovine serum FBS. The hybrid hydrogels were immersed in the complete culture medium for 24 h, at 37° C. before seeding. For static seeding of the cells, composite hydrogels were located in 24-well plate and 50 µl cell suspensions (3×105 cell/mL) were seeded onto the hydrogels. After 15 minutes, 1 mL of compete culture medium was added to each well. The hydrogels were placed in the incubator for 24 h, and CellTiter-Glo luminescent cell viability assay was used on days 1 and 4 to characterize the metabolic activity of cells. Standard curve was generated using ATP solutions at specific concentrations (1, 0.1 and 0.01 µM) prepared in cell culture medium. Next, 150 µl from each hydrogel medium was taken and placed in the same amount of CellTiter-Glo Reagent. Both ATP solutions and samples Were incubated at 25° C. for 15 minutes and then, luminescence was measured using a plate reader.

FIG. 2 shows the results of in vitro cell viability tests after seeding three types of pH responsive hydrogels on Mouse 3T3 Fibroblasts and incubating for 1-4 days. ATP amounts indicate that three types of hybrid hydrogels have no toxic effects on fibroblast growth. Better fibroblast viability was observed in the sample of pH responsive hydrogel with SBS particles.

Example 5

In vivo implantation experiments for irritation or intracutaneous reactivity tests with hybrid P(MAA-g-EG) hydrogels The ISO Standard defines irritation as a localized inflammatory response to a single or continuous application of the test sample. Here, the irritation test was used to assess the irritation potential of pH responsive P(MAA-g-EG) hydrogels. Fluid extracts from 0.2 g/mL (w/v) of the dried pH responsive hydrogel was directly applied on the right and left back skin of three healthy female New Zealand rabbits, and rabbits were incubated at 37° C. for 72 h. The right caudal zone of the back was used as positive control (90% lactic acid) whereas the left side was used as a negative control (physiological saline solution) At 1, 24, 48, and 72 hours after injection, the intracutaneous reaction was assessed using the evaluation criteria. The criteria of classification of the intracutaneous reactions (erythema and edema) are: 0-0.4 insignificant, 0.5-1.9 slight, 2-4.9 moderate, 5-8 severe.

Figure 7:
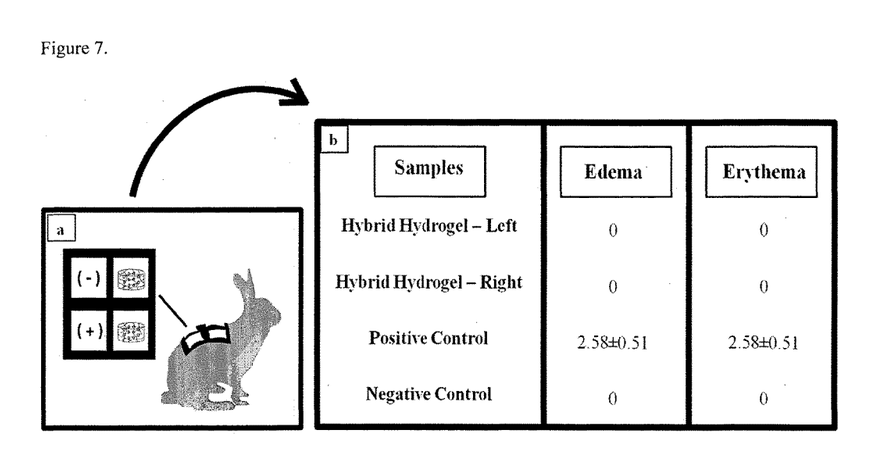
FIG. 7. In vivo implantation experiments for irritation with hybrid P(MAA-g-EG) hydrogels. Localized imflammatory response on the right and left back skin of three healthy female New Zealand rabbits which were incubated at 37° C. for 72 h.

The irritation assay demonstrated that, pH sensitive P(MAA-g-EG) hydrogel with SBS particles, did not result in any intracutaneous reaction such as erythema and edema in rabbits, when compared to the negative control at all the observation times of 1, 24, 48, and 72 h (as shown in FIG. 7(b)). This is a significant indication about the biocompatibility of pH responsive hydrogels synthesized with the approach developed here.

The invention claimed is:

1. A pH responsive hybrid hydrogel, wherein the pH responsive hybrid hydrogel is Styrene-Butadiene-Stene (SBS) incorporated poly(Methacrylic acid-grafted-Ethylene Glycol) p(MAA-g-EG), which is synthesized via visible light induced photopolymerization.

2. The pH responsive hybrid hydrogel of claim 1, wherein Eosin Y is used as a photo-initiator and Triethanolamine TEA) is used as a co-initiator in a synthesis.

3. The pH responsive hybrid hydrogel of claim 1, wherein incorporated Styrene-Butadiene-Styrene is either in a disc form or a crushed particle form.

4. A method of synthesizing a pH responsive hybrid hydrogel comprising a step of incorporating Styrene-Butadiene-Styrene (SBS) and poly(Methacrylic acid-grafted-Ethylene Glycol) (p(Maa-g-EG)) via visible light induced polymerization.

5. A method of synthesizing the pH responsive hybrid hydrogel of claim 4, further comprising using Eosin Y as a photo-initiator and triethanolamine (TEA) as a co-initiator.

6. The method of synthesizing the pH responsive hybrid hydrogel of claim 4, wherein the Styrene-Butadiene-Styrene is either in a disc form or a crushed particle form.

7. The method of synthesizing the pH responsive hybrid hydrogel of claim 4, comprising following steps:
   i. mixing monomers methacrylic acid (MAA), poly(ethylenglycol) monomethyl ether monomethacrylate (PEGMMA), and a crosslinking agent tetraetylene glycol dimethacrylate (TEGDMA) and adding a photo-initiator triethanolamine and a co-initiator eosin Y to a solution;
   ii. adding styrene-butadiene-styrene (SBS) either in a disc form or a crushed form to a mixture and shaking;
   iii. exposing a resulting solution to a visible light; and
   iv. washing with water and freezing dried.

8. The pH responsive hybrid hydrogel of claim 1, wherein the pH responsive hybrid hydrogel is used as a drug delivery agent for controlled release, sustained release or sequential release.

9. A pharmaceutical composition, comprising: a pH-responsive hybrid hydrogel according to claim 1, an active ingredient and pharmaceutically acceptable excipients.

10. The pharmaceutical composition of claim 9, the active ingredient is selected from the group consisting of gabapentin, lamotrigine, levetiracetam, ocarbazepine, pregabalin, tiagabine, topiramate and zonisamide, wherein the gabapentin, the lamotrigine, the levetiracetam, the oxcarbazepine, the pregabalin, the tiagabine, the topiramate and the zonisamide are anticonvulsant drugs.

11. The pharmaceutical composition of claim 10, wherein the active ingredient is pregabalin.

12. The pharmaceutical composition of claim 9, wherein the pharmaceutical composition is in a form of a tablet, a capsule, an intravenous formulation, an intranasal formulation, a transdermal formulation, a formulation for muscular injection, a syrup, a suppository or an aerosol.

13. The method of synthesizing the pH responsive hybrid hydrogel of claim 5, comprising following steps:
   i. mixing monomers methacrylic acid (MAA), poly(ethylenglycol) monomethyl ether monomethacrylate (PEGMMA), and a crosslinking agent tetraetylene glycol dimethacrylate (TEGDMA) and adding a photo-initiator triethanolamine and a co-initiator eosin Y to a solution;
   ii. adding styrene-butadiene-styrene (SBS) either in a disc form or a crushed form to a mixture and shaking;
   iii. exposing a resulting solution to a visible light; and
   iv. washing with water and freezing dried.

14. The method of synthesizing the pH responsive hybrid hydrogel of claim 6 comprising following steps:
   i. mixing monomers methacrylic acid (MAA), poly(ethylenglycol) monornethyl ether monomethacrylate (PEGMMA), and a crosslinking agent tetraetylene glycol dimethacrylate (TEGDMA) and adding a photo-initiator triethanolamine and a co-initiator eosin Y to a solution;
   ii. adding styrene-butadiene-styrene (SBS) either in a disc form or a crushed form to a mixture and shaking;
   iii. exposing a resulting solution to visible light; and
   iv. washing with water and freezing dried.

15. The pH responsive hybrid hydrogel of claim 2, wherein the pH responsive hybrid hydrogel is used as a drug delivery agent for controlled release, sustained release or sequential release.

16. The pH responsive hybrid hydrogel of claim 3, wherein the pH responsive hybrid hydrogel is used as a drug delivery agent for controlled release, sustained release or sequential release.

17. The pH responsive hybrid hydrogel of claim 1, wherein the pH responsive hybrid hydrogel is used as a drug delivery agent for controlled release, sustained release or sequential release.

18. The pharmaceutical composition of claim 10, wherein the pharmaceutical composition is in a form of a tablet, a capsule, an intravenous formulation, an intranasal formulation, a transdermal formulation, a formulation for muscular injection, a syrup, a suppository or an aerosol.

19. The pharmaceutical composition of claim 11, wherein the pharmaceutical composition is in a form of a tablet, a capsule, an intravenous formulation, an intranasal formulation, a transderrnal formulation, a formulation for muscular injection, a syrup, a suppository or an aerosol.

* * * * *